US006698421B2

United States Patent
Attolini

(10) Patent No.: US 6,698,421 B2
(45) Date of Patent: Mar. 2, 2004

(54) APPARATUS FOR NEBULIZING A LIQUID, IN PARTICULAR FOR MEDICAL USE

(75) Inventor: Lorenzo Attolini, Parma (IT)

(73) Assignee: Medel S.p.A., Parma (IT)

( * ) Notice: Subject to any disclaimer, the term of this patent is extended or adjusted under 35 U.S.C. 154(b) by 0 days.

(21) Appl. No.: 09/728,246

(22) Filed: Dec. 1, 2000

(65) Prior Publication Data

US 2001/0002592 A1 Jun. 7, 2001

(30) Foreign Application Priority Data

Dec. 3, 1999  (IT) ......................................... PR99A0090

(51) Int. Cl.[7] ............................................. A61M 11/00
(52) U.S. Cl. ........................... 128/200.14; 128/200.21; 128/200.17; 128/200.16; 239/338
(58) Field of Search ................... 128/200.21, 200.14, 128/200.17, 200.16; 239/338

(56) References Cited

U.S. PATENT DOCUMENTS

| 4,201,737 A | * | 5/1980 | Carden | 128/200.21 |
| 4,257,415 A | * | 3/1981 | Rubin | 128/200.21 |
| 4,456,007 A | * | 6/1984 | Nakao et al. | 128/200.21 |
| 4,949,715 A | * | 8/1990 | Brugger | 128/200.14 |
| 5,022,587 A | * | 6/1991 | Hochstein | 128/203.12 |
| 5,299,565 A | * | 4/1994 | Brown | 128/200.21 |
| 5,771,928 A | * | 6/1998 | Zepic et al. | 137/625.22 |
| 5,881,722 A | | 3/1999 | Cebielski et al. | |
| 6,158,431 A | * | 12/2000 | Poole | 128/203.12 |
| 6,176,234 B1 | * | 1/2001 | Salter et al. | 128/200.14 |
| 6,237,589 B1 | * | 5/2001 | Denyer et al. | 128/200.21 |

FOREIGN PATENT DOCUMENTS

| DE | 28 31 970 A | 2/1980 |
| DE | 93 09 886 U | 9/1993 |
| EP | 0 712 636 A | 5/1996 |
| FR | 2 690 360 A | 10/1993 |

* cited by examiner

Primary Examiner—Weilun Lo
Assistant Examiner—Darwin P. Erezo
(74) Attorney, Agent, or Firm—Michael Best & Friederich LLP

(57) ABSTRACT

An apparatus (1) for nebulising a liquid, in particular for medical use, comprises a box case (2) and a compressor assembly (4) housed internally to the box case (2) and provided with an air intake conduit (5) and an air delivery conduit (6). A device (10) for activating the compressor assembly (4) is housed internally to the box case (2) and is provided with an external command (16) which can be activated by the user. A nebulising bulb (17) is housed in the box case (2), presents a terminal mouthpiece (18) and is provided with an air inlet section placed directly in communication with the delivery conduit (6) of the compressor assembly (4).

20 Claims, 4 Drawing Sheets

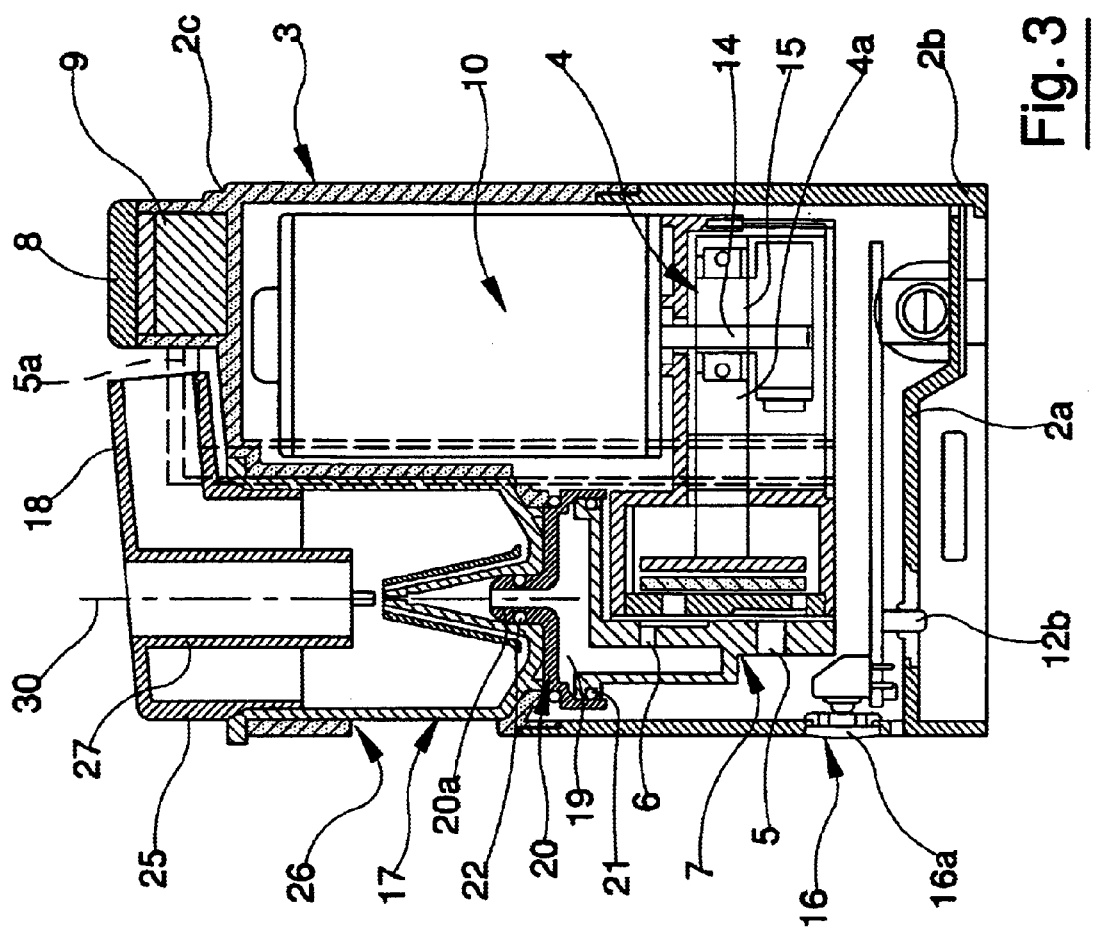
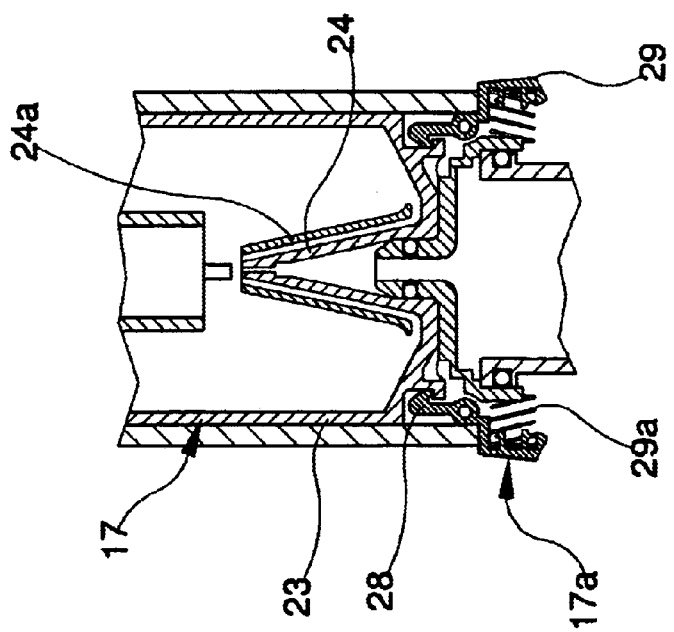

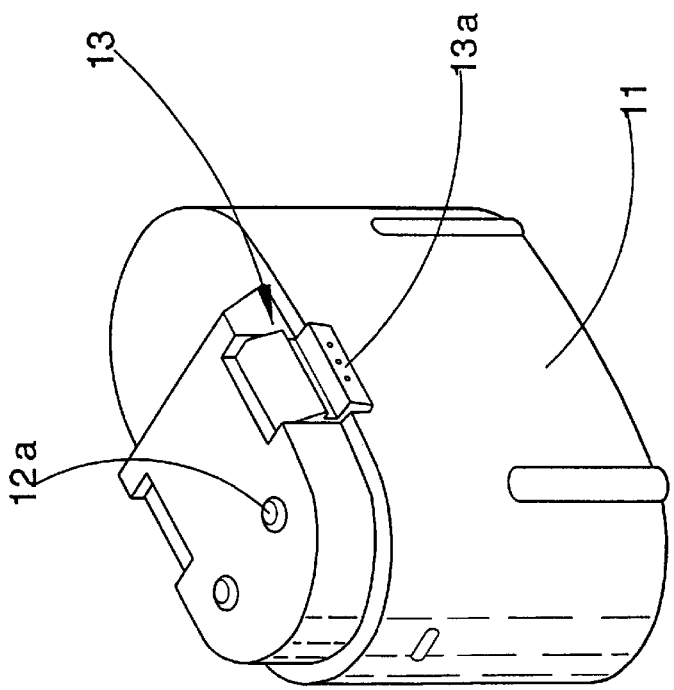
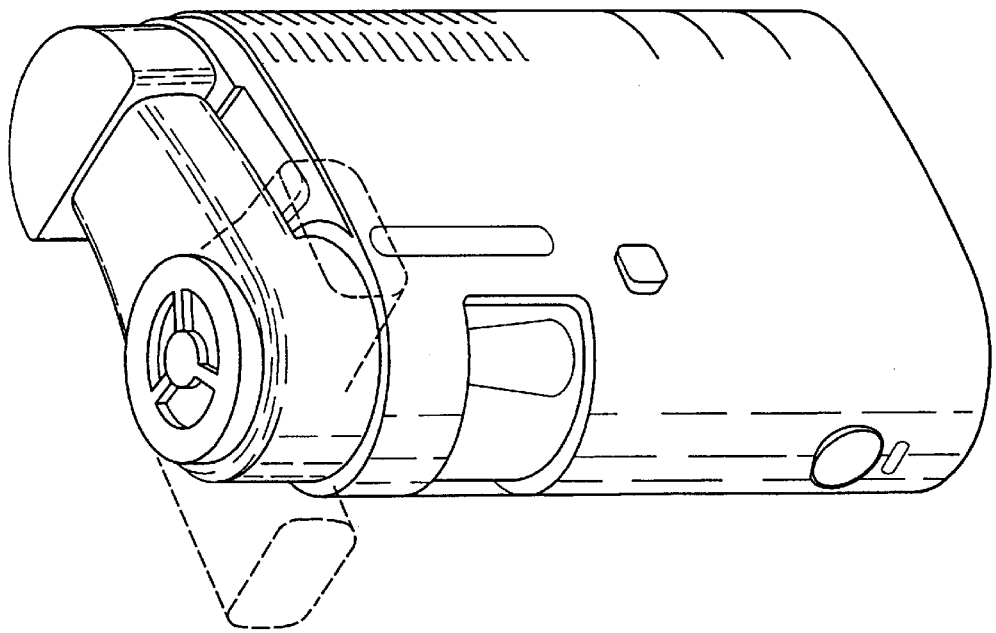
Fig. 5

APPARATUS FOR NEBULIZING A LIQUID, IN PARTICULAR FOR MEDICAL USE

BACKGROUND OF THE INVENTION

The present invention relates to an apparatus for nebulising a liquid, in particular for medical use.

As is well known, nebulising apparatuses are used in particular in the field of aerosol therapy, i.e. the therapeutic treatment of symptomatologies of the upper respiratory tract, such as asthmatic or bronchial symptomatologies. This therapeutic system provides for the generation of aerosol, i.e. a dispersion or nebulisation of particles of appropriate medical fluid whose action is effected by means of inhalation of the medical liquid itself. Such apparatuses are widespread and used mostly in the case of paediatric therapies, and they are provided in different formats able to meet the different requirements of the user. More specifically, nebulising apparatuses can also be produced in pocket formats, so that the user can, at any moment, have the necessary medication available, especially in case of conditions entailing frequent or difficult to predict respiratory crises, such as asthmatic conditions.

Mainly for home use, nebulising apparatuses of the pneumatic type are known, so defined because they comprise a compressor that aspirates air from the environment and sends it to a nebulising bulb containing the medical liquid.

The compressor is generally housed in a rigid container, made for instance of plastic material, which integrates the intakes of the aspiration and delivery conduits coming from the compressor itself. In use, the rigid case containing the compressor bears solidly on a plane whilst the nebulising bulb is placed in proximity to the user's face and is connected to the inlet of the delivery conduit by means of a flexible piping.

The compressor can comprise a head integrating both the intake and the delivery conduit, interfacing directly with the exterior by means of inlets obtained directly on the head itself and destined to adapt to the profile of the rigid containment case.

Such apparatuses present important drawbacks both in regard to the assembly phase and in regard to the employment phase of the apparatus itself.

Both the nebulising bulb and the connecting pipeline, together with any accessories, such as masks or others, are external to the rigid case and need to be housed separately relative to the apparatus or in portions of the case serving as a containment compartment. In either case the bulk of the apparatus, both in use and once stowed, is definitely greater than the dimensions actually required by the compressor and by the connections internal to the rigid case.

Moreover, the excessive bulk and the need for the connecting pipeline between the delivery inlet and the nebulising bulb limit use of the aforesaid apparatus as a substantially fixed station.

The aforementioned drawbacks also manifest themselves in the case of compressors comprising a head integrating both the intake conduit and the delivery conduit, although both structural complexity and dimensions are limited. Such apparatuses, too, are substantially provided exclusively for home use, in consideration of the fact that a connecting pipeline is always necessary between the delivery intake and the nebulising bulb.

Also known are nebulising apparatuses that exploit ultrasound devices with piezoelectric vibration systems, placed in communication with a tank of medical liquid in such a way as to generate vibrations with heavy amplitude within the liquid itself.

When the piezoelectric element is activated, the medical liquid undergoes an upward thrust, assumes a substantially cone-like shape and is nebulised against a deflector. This type of nebulising apparatus can be employed for home use or to obtain a pocket format apparatus.

Such apparatuses, however, have some drawbacks. In the first place, the ultrasound device generates a high dispersion in the dimensions of the nebulised particles of medical liquid, so that particles that are respectively too small and too large relative to optimal dispersion values are obtained. Based on the experience accumulated by the Applicant in the industry, this excessive dispersion generates reductions of the therapeutic effect of the nebulised medical liquid. Moreover, the use of an ultrasound device produces as-yet not fully known effects within the structure of the medical liquid, with consequent possible risks for the user's health.

SUMMARY OF THE INVENTION

The aim of the present invention is to eliminate the aforesaid drawbacks by making available an apparatus for nebulising a liquid, in particular for medical use and of the pneumatic type, which is able to adapt to a wide range of formats and which in particular allows to obtain a compact, pocket format, without accessories or pipelines outside the rigid containment case, in order to be available in each situation of need by the user.

Said aims are fully achieved by the apparatus for nebulising a liquid, in particular for medical use, of the present invention, which is characterised by the content of the claims set out below and in particular in that it comprises a nebulising bulb housed in the box case and presenting an inlet section placed directly in communication with the delivery conduit of the compressor assembly.

BRIEF DESCRIPTION OF THE DRAWINGS

This and other features shall become more readily apparent from the detailed description of two preferred embodiments illustrated, purely by way of non limiting example, in the accompanying drawing tables, in which:

FIG. 3 shows a section according to the straight lines III—III of FIG. 2;

FIG. 4 shows a detail sectioned according to the straight lines IV—IV of FIG. 2;

FIG. 5 shows a perspective view of the apparatus of FIG. 1 in some possible operative conditions;

DESCRIPTION OF THE PREFERRED EMBODIMENTS

With reference to the Figures, the reference number 1 globally indicates an apparatus for nebulising a liquid.

Figure 2:
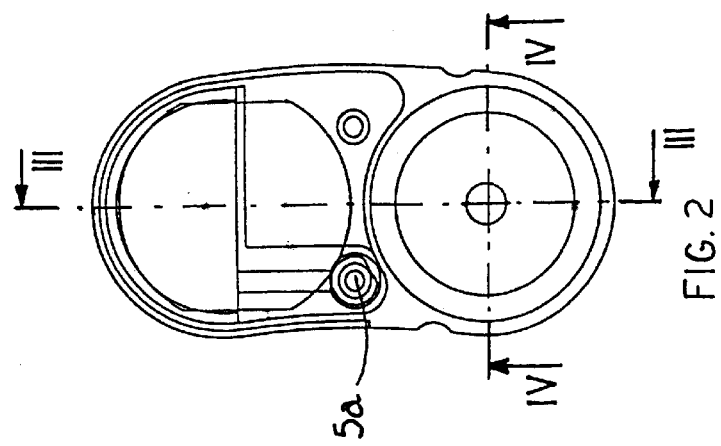
FIG. 2 shows a top view of the apparatus of FIG. 1.
Figure 1:
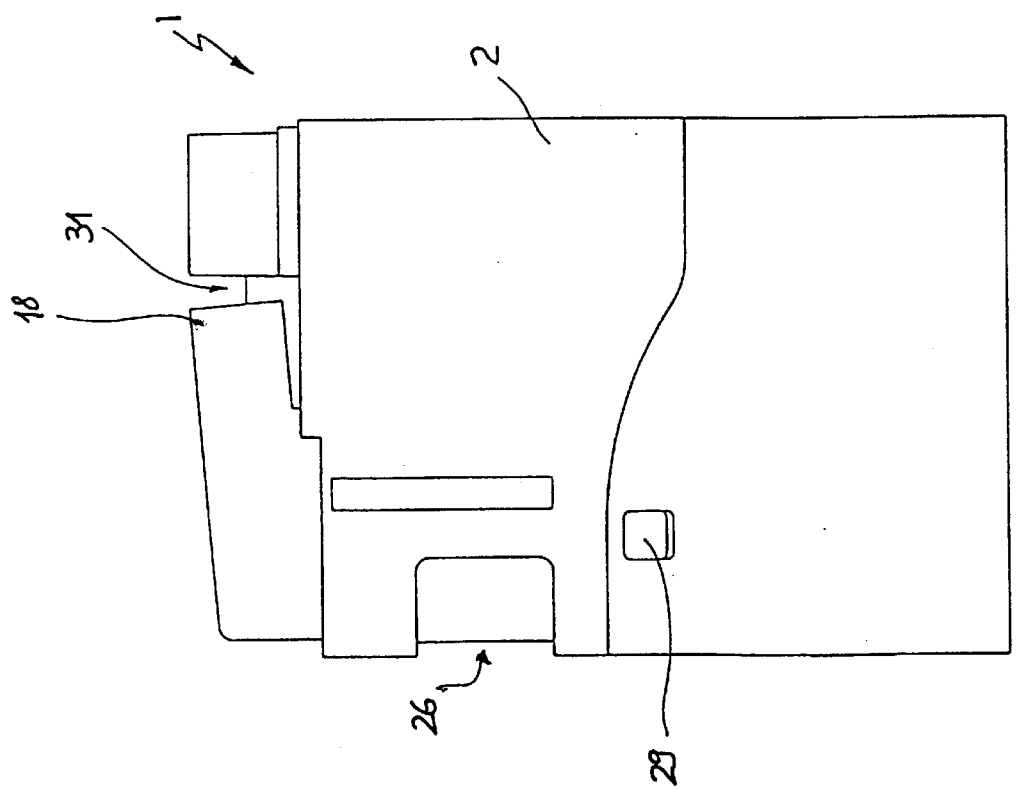
FIG. 1 shows a side view of an apparatus according to the present invention.

As shown in FIG. 1, the apparatus according to the present invention comprises a box case 2 made preferably of rigid plastic material, easily washable and impact-resistant. With particular reference to the figures, the box case can develop preferably but not necessarily with a transverse section presenting a greater axis and a lesser axis, i.e. with a bottom 2a, for instance with oval or rectangular development with rounded short sides, or curved oval, as shown in FIG. 2 to facilitate the user's grip.

From the bottom 2a a lateral wall 2b constituting the flanks of the apparatus 1 extends perpendicularly. The lateral wall 2b can present a facilitated grip area 3, developing along a portion of the lateral wall itself corresponding to one of the short sides of the cross section.

According to an embodiment, the facilitated grip area 3 can be realised by means of ribs obtained directly in the mould of the case or by adding anti-skid material or by means of horizontal knurls. In FIG. 5 the facilitated grip area 3 presents both the ribs 3a and the knurled area 3b.

The box case 2 superiorly comprises a lid, not shown herein, which interacts with a housing 2c.

Internally to the box case 2 is housed a compressor assembly 4. According to the illustrated embodiment the compressor assembly is positioned on the bottom 2a of the box case 2.

The compressor assembly 4 is of a substantially known type, hence it is not described in detail herein, and it is provided with a piston 4a translating along its own axis between a bottom dead centre and a top dead centre corresponding to the inversion of the air flow between an intake conduit 5 and a delivery conduit 6 and vice versa. Said inversion is produced by a membrane, interposed between the piston 4a and the intake conduits and the delivery conduit 6.

The compressor assembly 4 advantageously comprises a head 7 integrating both the intake conduit 5 and the delivery conduit 6. FIGS. 2 and 3 clearly show the development of the intake conduit 5 which presents an extremity 5a in connection with the exterior and advantageously positioned on the upper part of the box case 2 to be preserved from the external environment by inserting the lid on the box case 2.

The extremity 5a of the intake conduit 5 comprises a lid 8 which allows access to the intake conduit 5 and internally locks a filter 9 servicing also as a sound-proofing element.

The delivery conduit 6 is integrated in the head 7 and ends internally to the box case 2.

The apparatus 1 further comprises a device 10 for activating the compressor assembly 4, housed internally to the box case 2. The activation device 10 is of a known type and it can comprise a power supply unit for instance obtained by means of batteries 11, replaceable or rechargeable by means of a connector.

The apparatus can be connected directly to mains power or to a power source such as the cigarette lighter of a car.

In the embodiment shown in FIG. 5, the batteries 11 present two contacts 12a interacting with two contacts 12b inside the box case 2 and advantageously comprise a coupling device 13 interacting with the bottom 2a of the box case 2. This coupling device can be activated by the user by means of two push buttons 13a that project outwardly from the walls of the battery 11.

The activating device 10 presents a control shaft 14 operatively connected, by means of an eccentric 15, to the piston 4a of the compressor assembly 4 to impart the alternating translation motion thereto.

The activating device 10 further comprises an external command 16 which can be activated by the user. In the embodiment shown in FIG. 1, the external command 16 comprises a pushbutton 16a positioned on the lateral surface 2b of the box case 2.

The apparatus 1 further comprises a nebulising bulb 17 having an air inlet section coming from the delivery conduit 6 of the compressor assembly 4 and provided with a terminal mouthpiece 18.

The nebulising bulb 17 is originally housed within the box case 2 and presents the inlet section directly in communication with the delivery conduit 6 of the compressor assembly 4, without any interposed pipelines.

Between the head 7 and the nebulising bulb 17 can advantageously be inserted a resonating chamber 19 to create a sound-proofing effect.

The resonating chamber 19 is delimited inferiorly by the head 7 and superiorly by a shaped element 20, coupled with the interposition of a seal 21 onto the head itself. The shaped element 20 superiorly comprises a tubular portions 20a extending externally from the walls of the resonating chamber 19 to enter the air intake section of the nebulising bulb 17, through the interposition of a seal 22. This tubular portion 20a also favours the centring of the nebulising bulb 17 inside the box case 2.

Moreover, the shaped element 20 can present a raised edge 20b for housing and centring the nebulising bulb 17. In FIG. 3, this raised edge is obtained in the walls of the box case 2.

The nebulising bulb 17 advantageously comprises a tank 23 for containing the liquid to be nebulised. This tank 23 is superiorly open and it is inferiorly provided with a nozzle 24 for the entrance of the air coming from the delivery conduit 6 of the compressor assembly 4. On the nozzle 24 is inserted a known cone 24a which deviates the flow of air and draws the liquid from the tank 23 through some channels not shown herein.

The nebulising bulb 17 further comprises a conduit 25 for dispensing the nebulised liquid. This conduit on one side is inserted on the tank 23 whilst on the other side it shapes the terminal mouthpiece 18 of the nebulising bulb 17.

In the housing area of the nebulising bulb 17, the box case 2 advantageously comprise a window 26 to check the level of the liquid in the tank.

The dispensing channel 25 incorporates a flue 27 for the entrance of the outside air which is mixed with the nebulised liquid and the air coming from the compressor assembly 4. Superiorly to the flue 27 is provided a check valve, whilst on the upper wall of the mouthpiece 18 can be provided a known valve. This valve is inserted on an opening obtained on the walls of the mouthpiece and it comprises a housing wherein an elastic element is inserted.

The elastic element operates between a closed position wherein it is in contact with the walls of the mouthpiece 18, so that the opening is shut, and an open position in which it is raised relative to the walls of the mouthpiece 18, so that the opening is in communication with the exterior.

The closed position of the elastic element and hence of the valve corresponds to the user's inspiration, during which air comes from the inlet flue 27 and is mixed to nebulised medical liquid. The open position instead corresponds with the user's expiration, in order not to disperse medical liquid.

The nebulising bulb 17 is advantageously mounted able to rotate about an axis 30, internally to the box case 2, and it can be extracted from the box case 2 to fill the tank 23. The extraction and insertion of the nebulising bulb 17 is facilitated by the presence of a coupling device 17a, shown in detail in FIG. 4, introduced into the lateral walls of the box container 2.

This coupling device comprises two hooks 28 which interact with the base of the nebulising bulb 17 and which are commanded by two controls 29 projecting from the box case 2. The locked position of the hooks 28 is guaranteed by the presence of elastic elements 29a.

In particular the nebulising bulb 17 operates between an employment position, in which the mouthpiece 18 projects relative to the dimensions of the box case 2, and a resting position in which the mouthpiece 18 is completely interior to the dimensions of the box case 2.

For this purpose the box case 2 advantageously comprises a recess 31 able to house the mouthpiece 18 in the resting position of the nebulising bulb 17.

According to a possible embodiment, the nebulising bulb 17 can rotate by 180°, so that the mouthpiece 18 in the employment position projects frontally relative to the box case 2 and on the opposite side relative to the facilitated gripping area 3. Alternatively, a 90° rotation can be provided so that the mouthpiece projects laterally relative to the box case 2.

The nebulising bulb 17, operating between the rest position and the employment position, can also realise the external command 16 of the activating device 10. In this case, the rotation of the nebulising bulb 17 commands the powering and shutting down of the apparatus 1.

According to the latter solution, an intermediate position can advantageously provided between the rest position and the employment position, defined also as "stand by" position, to ready the apparatus 1 for powering.

Figure 6:
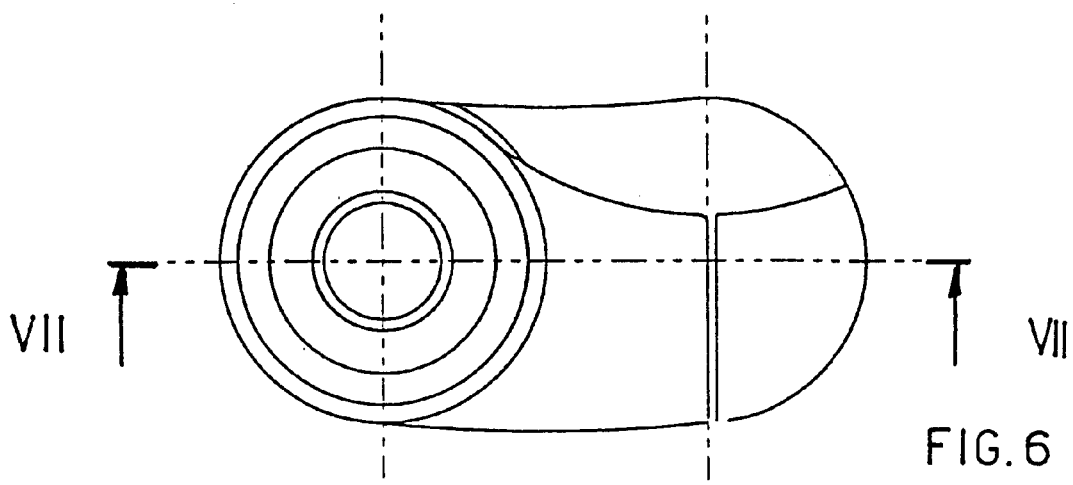
FIG. 6 shows a top view of an embodiment variation of the apparatus of FIG. 1.
Figure 7:
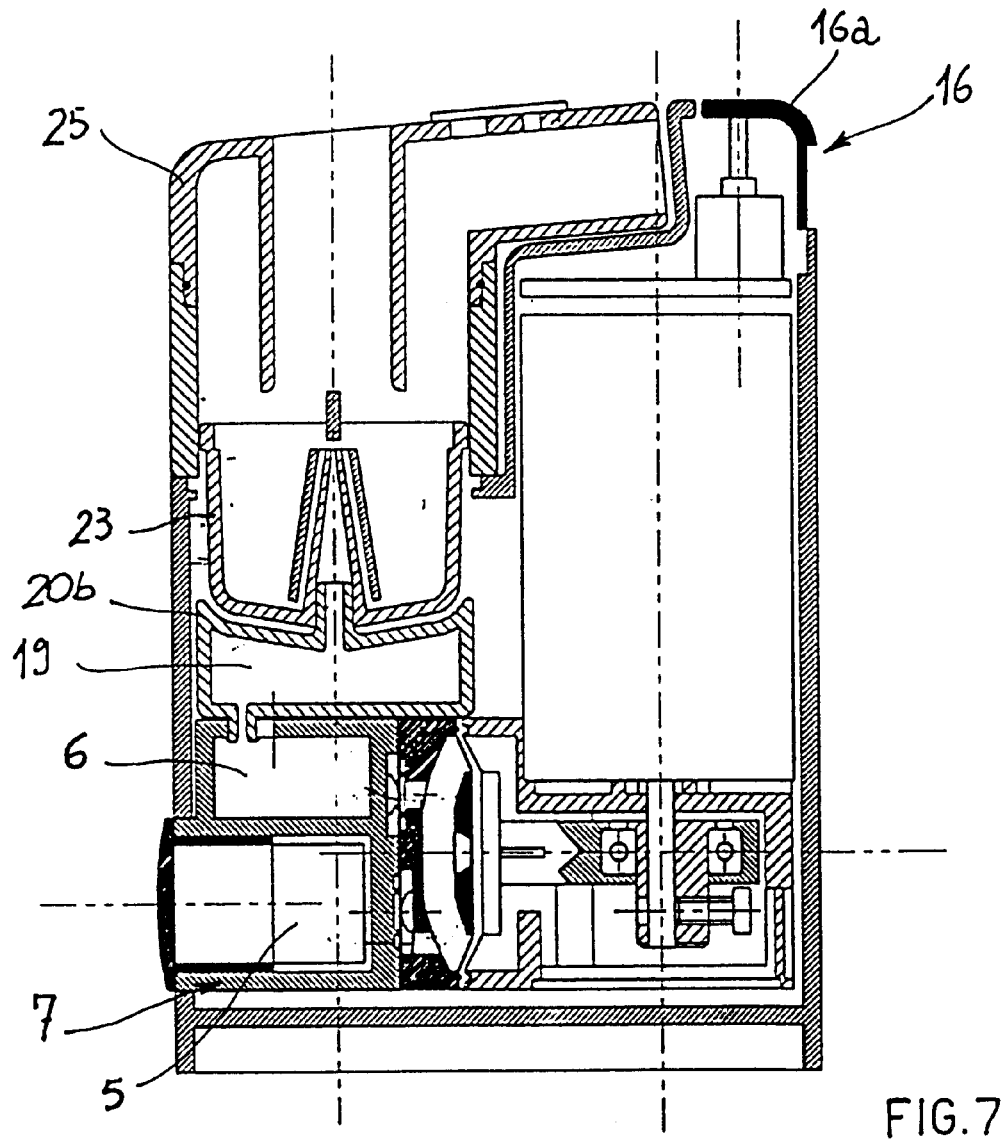
FIG. 7 shows a section view according to the straight lines VII—VII of FIG. 6.

The embodiment of FIGS. 6 and 7 presents some difference from the embodiment described above.

In regard to the compressor assembly 4, and in particular to the head 7, both the intake conduit 5 and the delivery conduit 6 are realised in the form of chambers internal to a single block constituting the head 7, also housed on the bottom 2a of the box case. The chamber shape of the two conduits allows to integrate in a single structure both the connecting function for the passage of the air flow, and the function of sound-proofing the entire compressor assembly contributing the lower the noise level of the apparatus. In the aforesaid variation the intake conduit 5 has a grip directly in communication with the exterior through an opening obtained on the lateral wall 2b of the box case 2. The delivery conduits 6 is parallel and side by side with the intake conduit 5 and it has an opening obtained in the walls of the head 7 and communicating with the volume internal to the box case 2.

In regard to the external command 16 of the activation device 10, the pushbutton 16a is positioned on the summit of the box case 2, preferably inserted at an end portion of the box case 2, corresponding to an extremity of the greater axis of the cross section of the box case itself, and it is positioned superiorly to the facilitate grip area 3 in such a way as to allow the apparatus to be gripped and controlled with a single hand.

The tank 23 can be extracted from the box case 2 to be filled or replaced and is inserted, inside the box case 2, into a compartment partially delimited by the lateral wall 2b in proximity with a lesser side of the cross section of the box case 2. This compartment can be accessed by removing the dispensing conduit 25 from the box element 2.

In both embodiments, the tank 23 can be realised both as a reusable container, preferably made of clear and washable plastic material, or by means of a single-dose cartridge, possibly comprising a lid to be removed prior to use.

In FIG. 7, the resonating chamber 19 presents an inlet section and an outlet section so positioned as to connect respectively with the delivery intake and with the nozzle 24 of the tank 23.

The inlet section of the resonating chamber 19 and the delivery intake can be coupled inside each other thereby allowing an immediate and correct positioning of the resonating chamber 19 relative to the head 7 of the compressor assembly 4. In particular, the inlet section can comprise a tubular portion extending externally relative to the walls of the resonating chamber 19 destined to be inserted into the delivery intake.

The resonating chamber 19 thus simultaneously serves the purposes of connecting the flow of air to the bulb, of sound-proofing the vibrations generated by the compressor assembly 4 and housing for the tank containing the liquid. If the tank 19 is obtained by means of a single dose cartridge, the tubular portion constituting the output section can advantageously comprise a device for perforating the bottom of the cartridge.

The operation of the apparatus according to the present invention is as follows. The nebulising bulb 17 can be extracted from the box case 2 and the dispensing conduit 25 is removed from the tank 23.

The tank 23 is filled with medical liquid or replaced with a single-dose cartridge and then stored on the resonating chamber 19, centring it relative to the outlet section and to the raised edge.

In the case of an apparatus 1 in pocket format, the user grips the apparatus itself in proximity to the facilitated grip area 3 and commands its starting by means of the pushbutton 16a or rotating the dispensing conduit 25.

The rotation of the dispensing conduit 25 makes the mouthpiece 18 project relative to the box case, so that the user can approach it to his/her respiratory tract to apply the therapy. The apparatus 1 as described above both in the structural sense and in the functional sense, finds application in particular in the medical field in the treatment of respiratory tract illnesses and it is realised preferably in a pocket format to meet emergency requirements or immediate needs above all in case of chronic illnesses and with sporadic and unpredictable respiratory crises, such as asthma. In any case, it is possible to envision a home use of the present apparatus for the treatment of illnesses which do not present critical situations and possibly require prolonged sessions.

Moreover, the present invention allows to obtain considerable advantages.

In the first place, it is possible to eliminate all junction pipes and in particular the pipeline connecting the delivery intake and the nebulising bulb. The structure of the apparatus 1 is thus compact and reduced in size, with no external elements and hence particularly suitable for a pocket format.

Moreover, the elimination of the pipelines and the presence of seats for the facilitated housing of the individual elements, simplifies both the assembly phase and the employment phase.

The original shape of the nebulising bulb allows its extraction to access the tank containing the liquid, facilitating both the filling or replacement phase and the cleaning phase and eliminating the risk of incrustations or residues, harmful for the therapeutic efficiency of the apparatus.

Moreover, compared with traditional pneumatic apparatuses, the apparatus 1 according to the present invention considerably lowers the noise level and emission of heat, thanks to the dual connecting and sound-proofing function served both by the intake and delivery conduits and by the resonating chamber.

What is claimed is:

1. An apparatus for nebulising a liquid, in particular for medical use, of the type comprising:
   a box case;
   a compressor assembly housed internally to said box case and defining an air intake conduit and an air delivery conduit;
   a device for activating the compressor assembly, housed internally to the box case and provided with an external command which can be activated by the user; and
   a nebulising bulb having an inlet section for the air coming from said delivery conduit of the compressor assembly and provided with a terminal mouthpiece;
   wherein said nebulising bulb includes a tank and is housed in the box case with said inlet section placed in communication with the delivery conduit of the compressor assembly;
   wherein said nebulising bulb, operating between a rest position and an employment position, realizes the external command of said activating device, so that a motion of the nebulising bulb commands the powering or shut-down of the apparatus; and wherein said nebulising bulb and said tank can rotate between said rest position and said employment position; and wherein said nebulising bulb, operating between said rest position and said employment position activates a pushbutton that realizes the external command of said activating device, so that the motion of the nebulising bulb commands the powering or shut-down of the apparatus.

2. An apparatus as claimed in claim 1, wherein said compressor assembly comprises a head integrating said intake conduit and said delivery conduit.

3. An apparatus as claimed in claim 1, wherein said intake conduit has an end in contact with the external environment positioned in the upper area of the box case.

4. An apparatus as claimed in claim 1, wherein said nebulising bulb can rotate by 90°, so that said mouthpiece projects laterally relative to said box case.

5. An apparatus as claimed in claim 1, wherein said nebulising bulb can rotate by 180°, so that said mouthpiece projects frontally relative to said box case.

6. An apparatus as claimed in claim 1, wherein said box case comprises a recess to house said mouthpiece in the rest position.

7. An apparatus as claimed in claim 1, wherein said nebulising bulb is mounted removable internally to said box case.

8. An apparatus as claimed in claim 1, wherein said box case has a coupling device for inserting and extracting the nebulising bulb.

9. An apparatus as claimed in claim 8, wherein said coupling device has at least a hook, operatively associated internally to the lateral walls and interacting with a base of the nebulising bulb, and at least a command projecting from the box case and operatively connected to said hook.

10. An apparatus as claimed in claim 1, wherein a resonating chamber is interposed between said delivery conduit and said nebulising bulb to serve simultaneously the connecting and sound-proofing functions.

11. An apparatus as claimed in claim 10, wherein said resonating chamber is obtained by means of a shaped element interposed between the head and the nebulising bulb.

12. An apparatus as claimed in claim 10, wherein said resonating chamber has a raised edge for housing the nebulising bulb.

13. An apparatus as claimed in claim 10, wherein said resonating chamber has a tubular portion extending externally from the walls of the resonating chamber itself to be inserted internally to the inlet section of the nebulising bulb.

14. An apparatus as claimed in claim 1, wherein said device for activating has at least a battery removably connected to the box case through a coupling device.

15. An apparatus as claimed in claim 1, wherein said box case defines a facilitated grip area.

16. An apparatus for nebulising a liquid, in particular for medical use, of the type comprising:

a box case;

a compressor assembly housed internally to said box case and defining an air intake conduit and an air delivery conduit;

a device for activating the compressor assembly, housed internally to the box case and provided with an external command which can be activated by the user;

a nebulising bulb having an inlet section for the air coming from said delivery conduit of the compressor assembly and provided with a terminal mouthpiece;

wherein said nebulising bulb includes a tank and is housed in the box case with said inlet section placed in communication with the delivery conduit of the compressor assembly;

wherein said nebulising bulb, operating between a rest position and an employment position, realizes the external command of said activating device, so that a motion of the nebulising bulb commands the powering or shut-down of the apparatus; and wherein said nebulising bulb and said tank can rotate between said rest position and said employment position; and a tank for containing the liquid to be nebulised provided with a nozzle for the entrance of the air coming from said delivery conduit of the compressor assembly; and a dispensing conduit for dispensing the nebulised liquid mounted on said tank and provided with said terminal mouthpiece.

17. An apparatus as claimed in claim 16, wherein said tank is constituted by a single-dose cartridge.

18. An apparatus as claimed in claim 17, wherein said mouthpiece has a valve opening between a closed position, during the user's inspiration, and an open position during the user's expiration.

19. An apparatus as claimed in claim 16, wherein the dispensing conduit incorporates a flue for the entrance of the external air.

20. An apparatus for nebulising a liquid, in particular for medical use, of the type comprising:

a box case;

a compressor assembly housed internally to said box case and defining an air intake conduit and an air delivery conduit;

a device for activating the compressor assembly, houses internally to the box case and provided with an external command which can be activated by the user; and a nebulising bulb including a tank and having an inlet section for the air coming from said delivery conduit of the compressor assembly and provided with a terminal mouthpiece; said nebulising bulb housed in the box case with said inlet section placed in communication with the delivery conduit of the compressor assembly; and a resonation chamber is interposed between said delivery conduit and said nebulising bulb to serve simultaneously connecting and sound-proofing functions; said resonating chamber including a tubular portion extending externally from walls of the resonating chamber itself to be inserted internally to the inlet section of the nebulising bulb, wherein said nebulising bulb has a tank for containing the liquid to be nebulised provided with a nozzle for the entrance of the air coming from said delivery conduit and the tank includes a cartridge; and wherein said tubular portion has a device for perforating the bottom of the cartridge.

* * * * *